United States Patent [19]

Miles

[11] 4,087,248
[45] May 2, 1978

[54] MULTIPLE ASSAY MACHINE AND METHOD

[76] Inventor: Laughton E. Miles, 1095 Vernier Pl., Stanford, Calif. 94305

[21] Appl. No.: 708,786

[22] Filed: Jul. 26, 1976

[51] Int. Cl.$^2$ .................... G01N 33/16; G01N 23/10
[52] U.S. Cl. ............................... 23/230 B; 23/230.6; 23/253 R; 23/259; 424/1; 424/1.5
[58] Field of Search ............... 23/253 R, 259, 230 B, 23/230.3, 230.6; 195/127; 424/1, 1.5

[56] References Cited

U.S. PATENT DOCUMENTS

| 3,754,863 | 8/1973 | Reunanen ..................... 23/230.6 X |
| 3,832,135 | 8/1974 | Drozdowski et al. ............ 23/253 X |
| 3,951,605 | 4/1976 | Natelson ........................... 23/259 X |

Primary Examiner—R.E. Serwin
Attorney, Agent, or Firm—Townsend and Townsend

[57] ABSTRACT

Method and apparatus are provided for carrying out simultaneous multiple manipulations. The method and apparatus are particularly directed toward heterogeneous (two phases) immunoassays, particularly radioimmunoassay (RIA) and immunoradiometricassays (IRMA and 2-site IRMA). These assays are primarily concerned with the determination of antibodies and immunologically active compounds (antigens and haptens). The device has a plurality of syringes mounted so as to allow for simultaneous and identical movement of the syringe plungers. In addition, means are provided for mounting open tubes, which are employed as solid phase reagents, to the ends of the syringes for the aspiration and discharge of unknown samples, reagents and wash solutions. A reservoir is provided in an upper portion of the apparatus for receiving solutions or dispensing solutions to the syringes. Individual assays may be carried out by using a single syringe and carrying out the process steps by transfers of solutions through a hollow tube.

31 Claims, 7 Drawing Figures

MULTIPLE ASSAY MACHINE AND METHOD

BACKGROUND OF THE INVENTION

1. Field of the Invention

The use of immunoassays for the detection of physiological compounds of interest has received increasing application as diseased states are found to relate to the presence or absence of compounds or the concentration of a particular compound. Because of the great sensitivity with which radioactive tracers can be measured, radioimmunoassay has found and is continuing to find widespread use for the detection and assay of haptens and antigens. Radioimmunoassays are carried out by mixing the compound of interest with a radioactive analog. These two species then compete for binding to a limited amount of antibodies. Antibody-bound radioactivity is separated from the "free" radioactivity by a variety of physio-chemical methods, and either the "bound" or the "free" radioactivity is measured. In one variant, solid-phase antibody is used, so that unreacted "free" radioactivity can be simply washed away.

There are two closely-related reagent-excess assay systems, the Immunoradiometric assay (IRMA) and 2-site IRMA. In these systems excess labelled antibody is used to convert the unknown into a directly detectable product. Unreacted labelled antibody is discarded. 2-site IRMA differs from IRMA in that the unknown substance is insolubilized during a preliminary reaction.

Immunoassays are subject to a wide variety of errors. Variations in temperature and reaction times can be critical. Most systems are highly sensitive to errors in the separation of "bound" and "free" labelled species (misclassification error), and manipulative techniques, such as the preparation, measurement and transfer of reagents (pipetting errors) are invariably important. Sophisticated assay variants using sequential and/or non-equilibrated reactions are especially vulnerable.

The concentration of the compound of interest in an unknown sample is determined by comparing the result obtained with the unknown, to the results obtained when assaying several solutions in which the concentration of the compound is known (a standard solution). It is therefore extremely important that all the assays be carried out in the same way with the same reagents.

There is a continuing need for a simple, accurate technique for carrying out immunoassays, whereby any deviations from the correct performance, such as variations in reaction times, differences in amounts transferred, and the like, will be minimized and common to the standards as well as the unknowns. Furthermore, such a system should aim for a minimum number of manipulations, especially those involving extraction, dilution and dispensing. When necessary or desirable, the system should be suitably rapid, and it should enable the accurate recording of results in relationship to the original sample. It should preferably be applicable to the estimation of material as diverse as small haptens and large proteins, be able to utilize both RIA and IRMA techniques, cope with equilibrated and sequential non-equibrated reactions, and effectively assay either large and small numbers in any given run. The procedures should also be economical and convenient.

At this time no automated assay machine fulfills all these criteria.

2. Description of the Prior Art

Various automated systems for measuring a variety of samples may be found in U.S. Pat. Nos. 3,469,438, 3,684,448 and 3,723,066.

In addition, there are a number of commercially available radioimmunoassay apparatuses. These include the Centria, supplied by Union Carbide Corporation, the LKB-Produkter, supplied by LKB, Sweden and the Darius, supplied by Digico Ltd., England.

Articles of interest are Miles, La Ricerce Clin. Lab. 5, 59 (1975), concerned with immunoradiometric assay methods; Cottrell et al, Clin. Chem. 21, 829 (1975) concerned with computer controlled automation of radioimmunoassays; Hersh and Yaverbaum, Clinica Chimica Acta 63, 69 (1975); and Jones and Worwood, J. Clin. Path. 20, 540 (1975) concerned with an immunoradiometric assay for ferritin.

SUMMARY OF THE INVENTION

Method and apparatus are provided for carrying out assays employing a member of one or two families of a pair of specifically bindable substances (SBS) in insolubilized form. Specifically bindable substances involve a pair: ligand; and receptor for the ligand. A receptor is any organic compound or composition which can differentiate, primarily by a significant difference in binding constant, its conjugate ligand from other compounds, normally organic, of similar structure.

For the most part, ligands will be haptens and antigens and receptors will be antibodies (antiligands) although other proteins and polysaccharides may also be employed as receptors.

Where antibodies are employed with conjugate haptens or antigens, these compounds will be referred to as immunologically bindable substances (IBS).

The apparatus employs a plurality of fixed syringes, with the syringe plungers connected for synchronous movement. Electronically controlled power means is programmed to move the plungers in accordance with a predetermined procedure. Mechanical or electronic means are provided for compensating for any slack in the movement of the plungers when reversing the direction. An overhead reservoir is preferably provided in fluid dispensing and receiving relationship with the syringes.

A complementary array of small conically-shaped open-ended tubes serve as syringe tips. The tips are delivered, stored and supported in a compact stack of interlocking tip support racks. The tips are inserted onto the syringes by pressing the syringe ends down into the tips of the support rack, with the tips supported by a special insertion block.

In carrying out the assay, the tips are activated by insolubilizing in the tips one of the members of an SBS pair. The tips may then be washed free of soluble material and may be stored or used directly. The solutions to be assayed are introduced into the tips from a multiple sample holder. The tips are immersed into the samples and the samples drawn into the tips by withdrawing the plungers. Reagents can be drawn up into the tips or may be introduced simultaneously as part of the sample solution or can be introduced from the syringes. Solutions in the tips can be ejected into a waste tray or withdrawn up into the syringes, all of the plungers moving synchronously, introducing solutions and expelling solutions from the tips simultaneously. For additional versatility in providing for reagent storage, either new or spent, an overhead reservoir can be provided, which communicates with the syringe cylinders through ports.

The reservoir can provide wash solutions, which may be introduced into the cylinders as needed, or the reservoir can receive spent sample or reagent solutions, by applying a mild suction.

After each operation or after the various reagents have contacted the tip interiors, and any washings carried out to remove unbound material, the tip ends and outer wall of the tips are wiped. By employing radioactive tracers as the reagent, and including standards in the sample tray to be simultaneously determined, the residual radioactivity in the tips can be related to the standard sample tips for direct determination of the unknown in the assay sample. The subject invention therefore provides a technique for carrying out assays simultaneously, whereby all the manipulative steps can be carried out with the unknowns and the standards synchronously, so that any errors introduced are constant for the standards and unknowns.

While the invention is primarily directed toward multiple simultaneous determination, the subject method also finds use for single determinations. By using a single syringe and tip, an assay can be rapidly carried out by the introduction and aspiration of reagents and wash solutions through the tip, which allows for concentration of samples, ease of reagent handling, and convenience in preparing the radioactive sample for counting.

The tip is extremely versatile in allowing for sampling of extremely small volumes in very small containers, while providing a surface for carrying out the various reactions required for the assay. The inner surface of the tip can be modified with projections to increase the surface area. Spacer arms can be provided in the tip, which can then be used for insolubilization of the analyte or reagent.

DESCRIPTION OF THE SPECIFIC EMBODIMENTS

In describing the subject invention, the assay will first be described generally, using immunoassays as illustrative, and then illustrated in relation to three different types of immunoassays involving radioactive tracer containing reagents: RADIOIMMUNOASSAY (RIA); IMMUNORADIOMETRICASSAY (IRMA) and 2-site IMMUNORADIOMETRICASSAY (2-site IRMA). The apparatus will then be described, including the ancillary equipment. The immunoassay will then be applied to the specific equipment, demonstrating the application of the equipment to the various immunoassays, which will then be followed by specific examples in which the equipment has been employed for the determination of specific compositions of interest.

I. ASSAY TECHNIQUES

The subject invention is concerned with the carrying out of assays with an SBS pair involving a ligand and a ligand specific receptor. Open ended tubes are employed, which allow for the introduction and removal of reagents, the flushing of the tubes to wash away undesired or superfluous material, and which permit easy, reproducible and simultaneous manipulation and an accurate final determination. In the broadest sense, the tubes are employed in assays wherein one of a specifically bindable substance pair (SBS), which includes haptens, antigens, antibodies, enzymes, enzyme substrates, serum proteins, etc. is insolubilized within the tube.

A reagent is provided which will bind to the insolubilized member of the SBS pair, and is, therefore, itself a specifically bindable substance, which has been modified so as to be capable of detection.

In assays, as a means for making a measurement, various atoms or compounds have been employed to provide the desired signal, such as radioactive atoms e.g. iodine, tritium, carbon, and the like; stable free radicals; enzymes; enzyme cofactors; fluorogenic substrates; bacteriophages; and fluorescers. The reagent which is employed for the assay determination will be referred to as the detectant. The distribution of the detectant between the solid phase and the liquid phase will be affected by the amount of compound to be measured, the analyte, which is present in the sample.

By providing for either a competition between the detectant and the analyte for the insolubilized member of the SBS pair, or by introducing consecutively the analyte followed by the detectant into the open ended tube, the amount of analyte present will affect the amount of detectant which is insolubilized. Depending upon the nature of the assay, either the amount of the detectant in the tube or in the liquid phase or both may be measured.

The tubes or tips which play a critical role in the subject invention can be composed of a wide variety of materials. The tubes need not be of a single material, the important aspect of the tube being the internal surface or packing in the tube. Either the innersurface or a packing or both may provide the surface upon which the member of the SBS pair is insolubilized.

The tips may be derived from a wide variety of polymeric materials, such as polyethylene, polypropylene, polyvinyl compounds, e.g. polyvinylchloride, polyacrylonitrile, polyacrylate, polymethacrylate, and copolymers thereof, polystyrene, nylon, polyterephthlate, cellulose, and the like. That is, naturally occurring polymers, particularly modified naturally occurring polymers, and synthetic addition and condensation polymers may be employed. Also, inorganic substances, such as glass may be used.

While conveniently, only the innersurface of the tip will provide the active surface for insolubilizing the member of the SBS pair, the tip can be conically shaped or partially blocked, so as to retain small particles or beads of the above indicated materials, which can serve independently or in conjunction with the tip inner-surface as the active area for insolubilization. Alternatively, an uneven surface e.g. projections, can be provided on the inner surface, such as ridges, mounds, or the like, to enhance the surface area.

Insolubilization can be achieved in a wide variety of ways. Depending upon the nature of the particular surface, as well as the nature of the member of the SBS pair to be insolubilized, absorption or adsorption may be satisfactory. In this mode, a solution containing the member of the SBS pair is drawn into the tip to allow for binding of the member to the surface. After sufficient time, the solution is expelled, and the internal surface of the tip washed with appropriate media, normally buffered media. In appropriate situations, the analyte from the unknown sample may be the insolubilized member of the SBS pair, being absorbed on the tip surface from the sample. Labelled receptor could be employed for detecting absorbed analyte.

Another technique is to covalently bond the member of the SBS pair to the surface. Spacer arms can be covalently bonded to the surface by various techniques known in the art leaving a functionality which is either active or can be activated to react with the member of the SBS pair. For example, nitriles can be modified to form imido esters, which will react with available amino groups on an antibody or antigen. There is an extensive literature concerned with the bonding of proteins to surfaces employing activated carboxylic acids, carbodiimides, imido esters, active alkyl halides, etc., to form amido, amidine, or amino linkages.

Alternatively, an immunological spacer arm may be employed. This involves either binding or bonding a member of the IBS pair to the surface which will then bind the complementary member of the IBS pair to the surface. Besides members of an IBS pair for binding, other materials include plasma binding proteins, tissue receptors, enzymes, co-factors, substrates, inhibitors and the like, in effect, any material which shows specificity for the analyte.

The small conical tips which are generally employed have a lower orifice of a diameter (I.D.) in the range of about 0.25 to 2mm, more usually in the range of 0.4 to 1mm. The height of the tip is not critical and can be varied with the desired volume of the tip. Usually the height of the tip will be from about 1 to 8cm, more usually from 2 to 5cm. The upper orifice which is mounted on the syringe is of a size to snugly fit the syringe barrel end and will generally have a diameter (I.D.) in the range of about 2.5 to 6mm. The thickness of the wall can be varied and is not critical to this invention. Conveniently, the thickness can vary along the wall, diminishing with diminishing inner diameter of the cone. A thickness range which provides the desired dimensional stability is from about 0.1 to 1.5mm, more usually from 0.2 to 1mm, where the thickness ratio from the top to the bottom of the tip can vary from 1:1 to 10:1. The volume of the tip is conveniently in the range of about 50 to 700µl, more usually 75 to 500µl.

While for the most part, the assays will involve combinations of IBS pairs, in those particular situations where the analyte of interest has specificity for a substance other than the other member of the IBS pair, there will be situations where it will be desirable to employ the related bindable substance. For example, if an enzyme substrate were to be determined, the enzyme and substrate could be used. Specifically, if one wished to determine NAD, one could prepare a tip having NAD bonded to the surface. By combining the sample with excess enzyme which employs NAD as a substrate, and then introducing the combination into the tip, only the enzyme which was bound to the NAD in the sample would not become bound to the tip surface. By expelling the solution from the tip, one could then determine the amount of enzyme which was not insolubilized.

The tips can be activated immediately prior to the carrying out of the assay or may be preprepared and stored. In storing the tips, normally mild temperatures will be employed, generally from about −40° to 25° C, and the tips will remain in a controlled environment so as to inhibit the deactivation of the insolubilized material. Conveniently, the inner surface of the tips may be coated with various liquids so as to maintain a moist polar environment. Illustrative materials are polyols, such as glycerol.

Depending upon the nature of the assay, the unknown sample may or may not be combined with additional reagents. In most cases, the sample will be appropriately buffered, so as to enhance binding, employing the usual buffers and providing a pH in or close to the physiological range. Where the assay requires that the annalyte bind to the detectant, so as to affect the number of available binding sites which can be insolubilized, the assay sample will normally be combined with the detectant reagent under conditions where such binding may occur. Where the detectant will become insolubilized to the degree the analyte has been insolubilized, normally the analyte will first be introduced into the tip, followed by the detectant reagent. After each introduction of a solution into the tip, the tip will normally be washed free of any materials which are non-specifically bound to the surface.

Various incubation steps may be involved where the tips are stored at ambient or under controlled conditions, usually at a temperature in the range of 15° to 40° C and at a humidity which prevents drying. Usually, the tips will be incubated after introduction of the analyte and, when the detectant is introduced separately, after introduction of the detectant. Incubation periods may vary from 0.5 to 12 hours depending on the particular compositions involved, concentrations to be detected, and the like.

The subject method finds specific advantage with dilute analyte solutions. By appropriate choice of the assay method, large excesses of the insolubilized member of the SBS pair may be employed. The analyte solution may then be drawn through the tip, whereby the analyte will be insolubilized by the excess insolubilized member bound or bonded to the surface. A controlled rate of drawing the solution through the tip and into the syringe can provide for relatively rapid quantitative removal of the analyte.

To further illustrate the method, three different assays employing radioactive tracers will be discussed generally. The first assay to be considered is RIA. In RIA, assuming antigen is the analyte, a competition is provided between a radioactively labelled antigen (detectant) and the antigen analyte. A limiting amount of antibody for the antigen is bonded to the innersurface of the tip. The unknown antigen solution is then introduced into the tip, either concurrently with the detectant or prior to introduction of the detectant. The advantage of introducing the two solutions consecutively, rather than as a single solution is that one may wash the tip free of any interfering materials in the unknown sample, prior to introduction of the detectant.

In addition, where the ligand and receptor are in a rapid equilibrium, the detectant and insolubilized member of the SBS pair may be preincubated before being combined with the analyte. This allows for preparation of the reagents in a convenient and reproducible form and may further reduce variations due to serum.

The next assay technique is referred to as IRMA. In IRMA, the unknown analyte is combined with a reagent comprising soluble purified radioactive antibodies (detectant). The tip has insolubilized analyte or a homologous analyte. The combined solutions of analyte and antibodies are drawn into the tip, where all free sites of the antibodies are bound to the insolubilized member of the IBS pair. A variation of the IRMA system is to use anti-globulin (anti(antiligand)) which is radioactively labelled (detectant). In this mode, the antibodies for the analyte are not labelled. After the analyte antibodies are insolubilized in the tip, the radio-actively labelled anti-globulin may then be introduced into the tip, so that the labelled anti-globulin will bind to any of the analyte antibodies which are insolubilized.

The third method is 2-site IRMA. In this method, antibodies for the analyte are insolubilized in the tip. The analyte is then introduced into the tip and becomes bound to the antibodies. It is required that the analyte be polyepitopic, that is, have at least two binding sites which permit the simultaneous binding of at least two antibody molecules. After the analyte is bound to the insolubilized antibody, unreacted antibody and other solutes washed away radioactively labelled antibody (detectant) for the analyte is introduced into the tip, which will bind to any insolubilized analyte. Alternatively, as described for IRMA, one can employ labelled anti-globulin (detectant), rather than labelled anti(analyte) so that the labelled anti-globulin can be used irrespective of the particular analyte.

In all the assays, after the labelled detectant has been introduced into the tip and become insolubilized, the solution is expelled or withdrawn from the tip, the inside of the tip washed with a convenient solution, normally a buffered solution to remove any non-specifically bound material and the ends of the tips wiped and blotted. This removes any residual fluid in the end of the tip and any material on the outside of the tip.

II. APPARATUS

The apparatus may be divided into three basic parts: (1) the syringe battery; (2) the electronically controlled motorized drive; and (3) ancillary equipment. The syringe battery will be considered first.

SYRINGE BATTERY

The syringe battery has a plurality of syringes uniformly arrayed in rows and columns in a housing, where the syringe cylinders or barrels are secured between two platforms, with the ends of the syringe cylinders extending beyond the lower platform. The upper platform may include a hollow portion which serves as a reservoir, with each of the syringes having one or more ports in fluid connection with the reservoir. Movably attached to the frame and situated beneath the lower platform is a plate through which the tip receiving ends of the syringes extend, which can be thrust downwardly to remove the tips from the syringe tip receiving ends and then retracted, so as to allow new tips to be mounted onto the syringe tip receiving ends. A connecting means is provided for connecting the plurality of plungers, with the plungers arrayed in complementary fashion to the syringe array, and extending into the syringe cylinders. The plungers are sufficiently long so as to be capable of traversing the length of the syringe cylinders and expelling all of the material from the cylinders. The plungers can be solid or hollow having a spring valve to allow for introduction of solutions into the syringes through the plungers.

ELECTRONICALLY CONTROLLED MOTORIZED DRIVE

The syringe battery is mounted in an electronically controlled motorized drive, which is shaped to receive the syringe battery, having an upper platform for housing the syringe plunger plate. The platform is mounted for vertical movement with concurrent movement of the syringe plunger plate. A lower supporting member is provided for supporting sample trays or reagent trays, which can be raised to the tips and then retracted. Obviously, as a less convenient alternative, one could lower the syringe battery to the sample platform. Restraining and supporting means is provided for rigidly holding the lower plate in position during the various operations. Driving means are provided for raising and lowering the upper and supporting member, which can be electronically controlled and programmed, so that the assay can be carried out substantially automatically. During the assay, it may be necessary to substitute sample trays.

ANCILLARY EQUIPMENT

A tip rack is provided which is a plate having a plurality of holes complementary to the spacing of the syringe array. Desirably, in addition to the holes for the tips a plurality of smaller holes are provided which are similarly spaced to the larger holes between the larger holes. In this way, the tips can be stacked with the smaller ends of the tips contained in the smaller holes, so that one has a staggered configuration, whereby a plurality of tip plates can be mounted one above the other. A large number of tips may then be stored in a relatively small area.

A second piece of equipment is referred to as an insertion block. The block has a plurality of complementary-shaped chambers for receiving and holding the smaller ends of the tips, providing mechanical support for the tips. The insertion block is employed when the tips are mounted on the tip receiving ends of the syringes by pressing the syringes into the tips supported by the block.

A third piece of equipment is referred to as a storage support box, which provides a humidity controlled environment which may also be thermostatted as desired.

Figure 1:
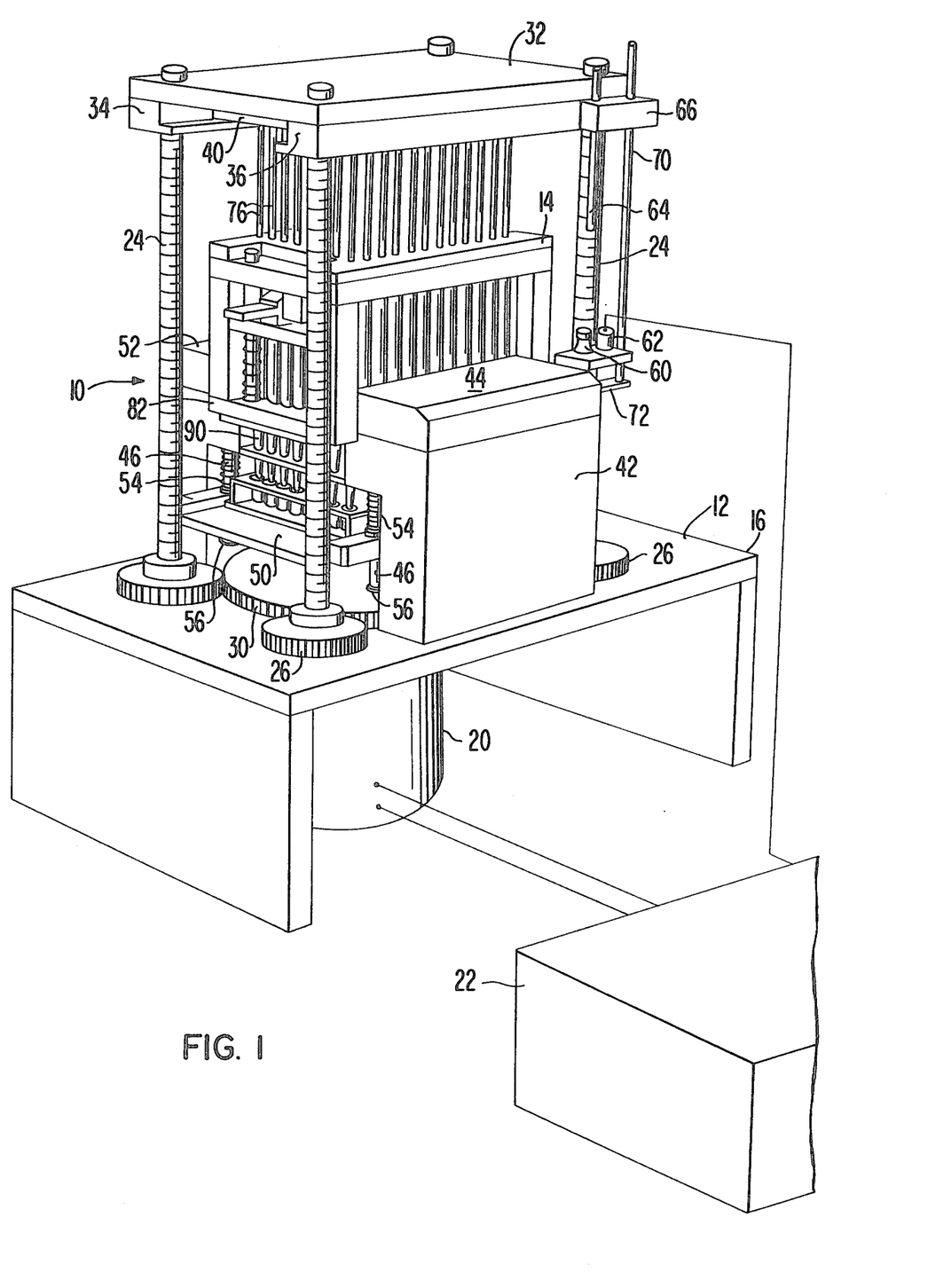
FIG. 1 is a perspective view of the syringe battery mounted in the motor driven control mechanism.

For further understanding of the apparatus, the drawings will now be considered. A multiple assay machine 10 is provided having a motor driven housing 12 and a syringe battery 14 as depicted in FIG. 1. The motor driven housing 12 has a supporting frame 16 under which is mounted motor 20, which is electronically controlled by programmer 22. Rotably mounted on platform 12 are four threaded bolts 24, which are seated on gears 26. Central gear 30 is driven by motor 20 and simultaneously drives gears 26.

An upper platform 32 is threadably mounted on threaded bolts 24 so as to be capable of vertical movement with the turning of the bolts. Upper platform 32 has symmetrically situated L-shaped arms 34 and 36 for receiving and securely retaining syringe plunger plate 40. Side walls 42 are mounted on platform 12 on opposite sides of syringe battery 14. Shoulders 44 extend inwardly from the walls and act to support the syringe battery 14 and lock the syringe battery in position. Extending downwardly from shoulders 44 are guides 46 on which a lower platform is movably mounted. The lower platform is affixed to a cam, not shown, which has cam arm 52 for raising and lowering the lower platform. Springs 54 are mounted on guides 46 to retract the lower platform 50. Stops 56 are provided on each of the guides to maintain the lower platform above the central gear 30.

Safety switches 60 and 62 are provided to control the extent of vertical movement of the upper platform 32. Post 64 is mounted in bracket 66 so as to engage safety switch 60 to control the extent to which upper platform 32 may be lowered. Post 70 also mounted in bracket 66 has arm 72 which engages safety switch 62 to control the extent of upper movement of upper platform 32. The two normally closed safety switches, 60 and 62 are operably connected to control mechanism 22 so as to shut the motor 20 off when the switches are engaged.

Figure 2:
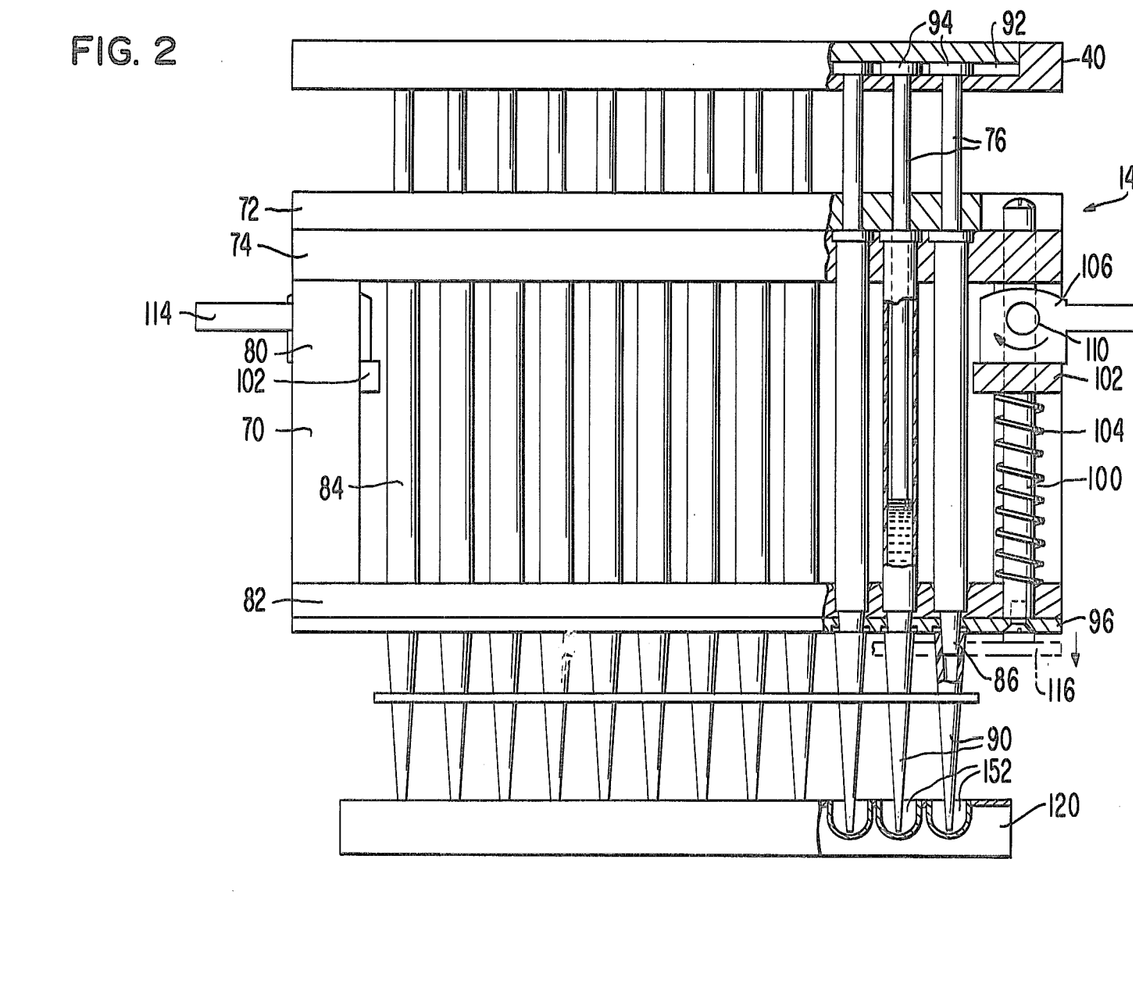
FIG. 2 is a front elevational view, partially in section of the syringe battery in contact with a sample plate.
Figure 4:
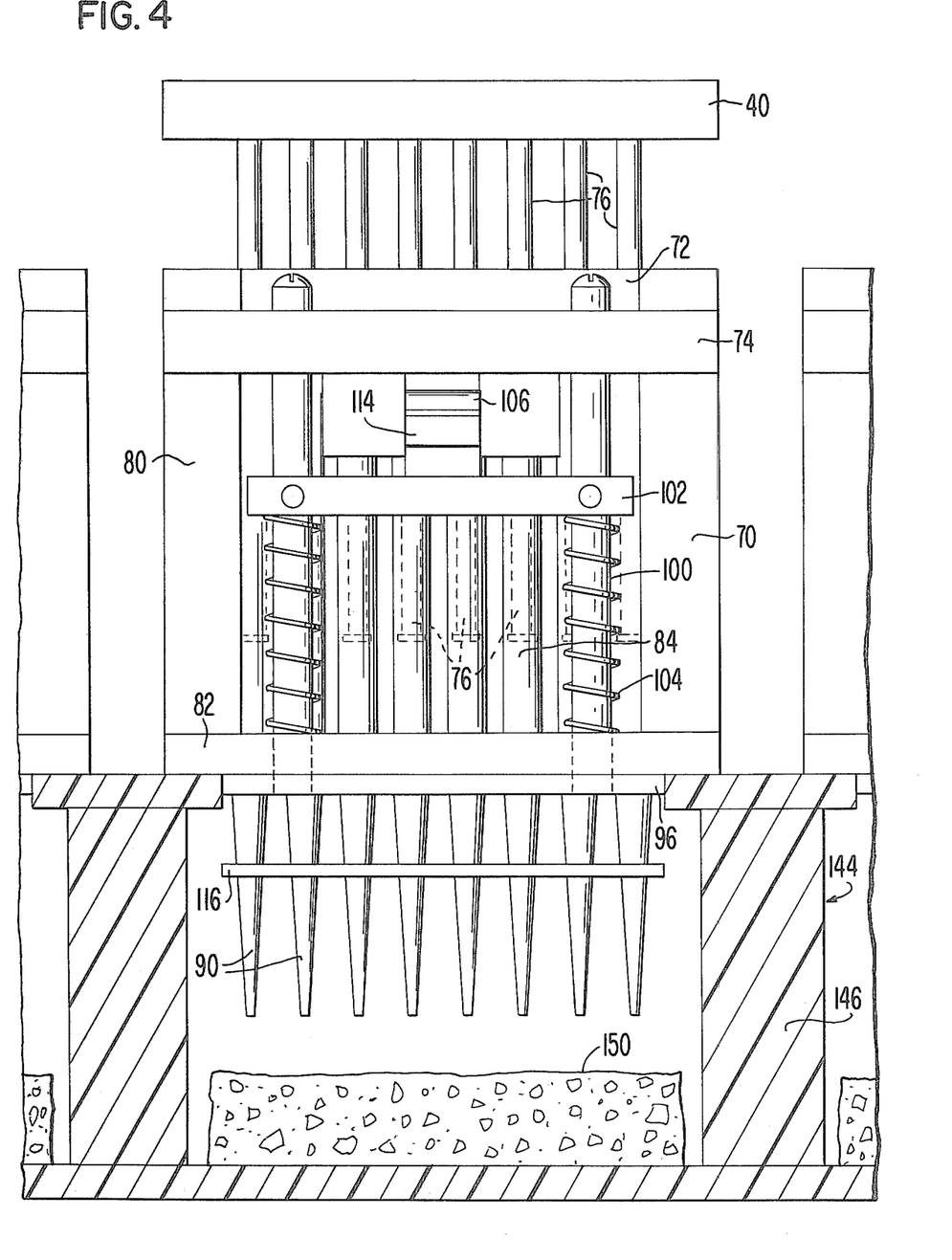
FIG. 4 is a side elevational view of a syringe battery during storage.

Turning now to FIGS. 2 and 4, the syringe battery 14 will be considered in further detail. The syringe battery 14 has a rectangular housing 70 with an upper guide plate 72 mounted on housing ceiling 74. The guide plate has a plurality of channels for guiding plungers 76. Ceiling 74 may have similar channels or may be hollow and serve as a reservoir for a solution, particularly a wash solution. This will be discussed in further detail subsequently. Supporting posts 80 support the ceiling 74 and are mounted on floor 82, which serves in conjunction with ceiling 72 to hold syringes 84 in position. Floor 82 is rigidly held in position by side walls 42 and shoulders 44. The tip receiving ends 86 of the syringes 84 extend through and beyond floor 82, providing sufficient length, so that the tips 90 may be securely attached to the syringe ends 86.

The syringe plunger plate 40 has a hollow center 92 for receiving the plunger heads 94 and holding the plunger heads in fixed position.

Ejection plate 96 is secured at its four corners to rods 100. At each end of the syringe battery 14 are bars 102. Springs 104 are mounted on the rods 100, between bar 102 and floor 82 so as to maintain upward pressure against the bar 102. Cam 106 is rotably mounted on pin 110 in yolk 112 and is moved by means of cam arm 114. By rotating the cam 106, the ejection plate 96 is moved downwardly as shown in phantom 116 so as to force the tips 90 off of the tip receiving ends 86 of the syringes. The rods 100 extend upwardly and through the ceiling 74, so as to remain aligned and not bind during movement.

The tips 90 are arranged in a rack 116 for storage and during use in the assay machine 10. The rack 116 permits all of the tips to be mounted on the tip receiving ends 86 simultaneously and be ejected simultaneously, while being maintained in the order in which they are originally organized.

A sample or reagent tray 120 is provided which has complementary cups for providing reagents to the tips or receiving reagents aspirated from the tips.

Figure 3:
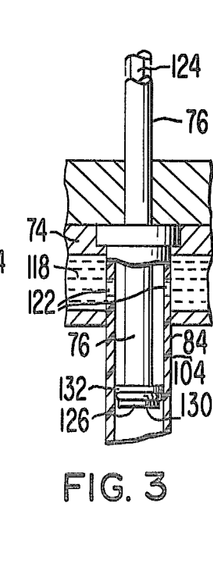
FIG. 3 is a partial elevational view in cross-section of a hollow plunger.

During the assay, it is desirable to minimize the manual manipulation or attention by an operator. Therefore, it is desirable that solutions, reagents, and the like, may be fed automatically to the tips 90. Turning to FIG. 3, the ceiling 74 is shown as hollow having reservoir 118. The reservoir 118 is in fluid connection with the syringes 104 through orifices 122. When the plunger 76 is moved above the orifices, fluid from the reservoir will enter the syringe 104, applying positive pressure to the reservoir as required to force fluid into the syringe, and may then be expelled from the syringe 76 into the tips 90 by moving the plunger downwardly. Alternatively, a hollow plunger may be employed having a central post 124 which is spring mounted and connected to foot 126. An O-ring 130 is compressed between the foot 126 and projection 132 which is rigidly attached to the plunger 76. The foot 126 is shaped to leave a gap between the foot 126 and the inner wall of the syringe 76. The O-ring 130 provides a seal with the inner wall of the syringe 84. By pressing on the central post 124, the foot 126 is lowered so as to provide fluid connection between the hollow center of the plunger 76 and the syringe 84. Fluid can therefore be dispensed by means of the plunger or withdrawn from the syringe employing suction. These types of plungers are commercially available and are referred to as Eppendorfer Syringes.

ANCILLARY EQUIPMENT

Figures 5, 6:
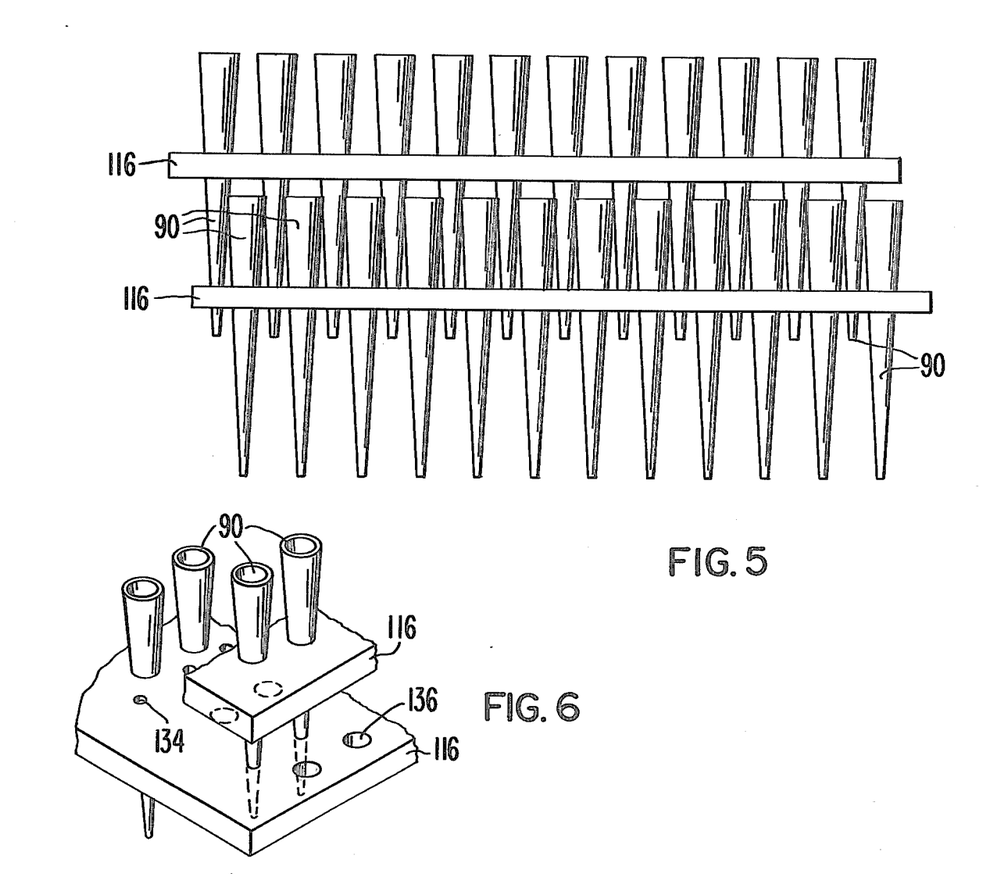
FIG. 5 is a front elevational view of the tips mounted in overlaying racks.
FIG. 6 is a fragmentary perspective view of the mounted tips depicted in FIG. 5.

The rack 116 has already been indicated as a means for spacing the tips 90 in conformity with the syringes 84. The racks also serve for storage and transporting the tips. In addition, as depicted in FIGS. 5 and 6, the rack may have a plurality of small holes 134 arrayed symmetrically in the same manner as the larger tip holding holes 136. By providing both of these openings, racks of tips may be stacked overlying each other, with the small holes orienting and supporting the tips in the next upper rack.

Figure 7:
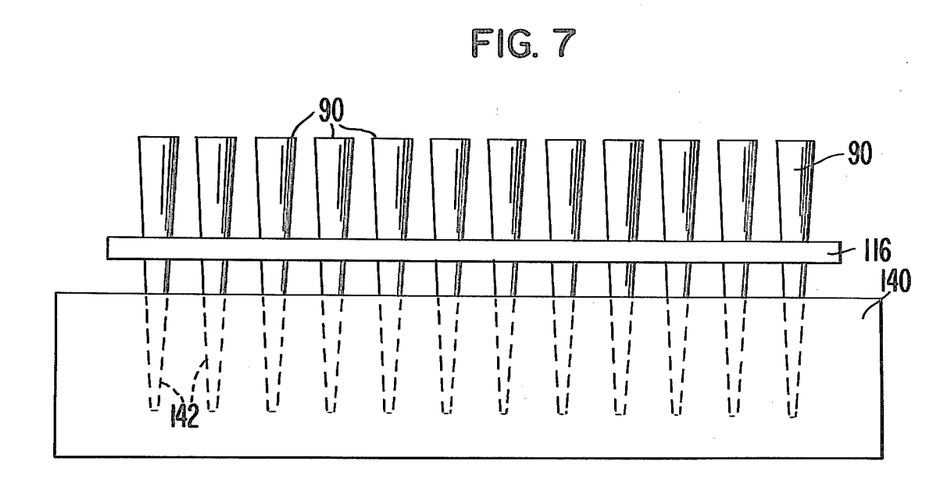
FIG. 7 is a front elevational view of the tips mounted in a rack and supported by an insertion block.

Also desirable is tip injection block 140 as depicted in FIG. 7. When mounting the tips 90 on the tip receiving ends 86 of the syringes 84, the tips are housed in conical bores 142, which provide mechanical support for the tips. Thus, substantial pressure can be applied to the tips to ensure that the tips are fixedly attached to the syringe ends.

The tips 90 are small, with the wall thickness sufficient to provide substantial mechanical stability to the tips.

ILLUSTRATIVE PERFORMANCE OF AN IMMUNOASSAY

As a further illustration of the subject invention, a multiple assay will be performed with the multiple assay machine. For illustrative purposes only, a 2-site IRMA assay will be employed.

A plurality of tips 90 are organized in a tip rack 116. The holes of the racks are complementary with the positioning of the syringes 104 in the syringe battery 14. Not all of the holes need be used, since the technique and apparatus do not require that all of the syringes in the syringe battery be employed.

Normally, standard solutions of the analyte and samples are prepared, carrying out any dilutions as may be required. The various standards and assay samples are introduced into the cups of an assay tray 120. The preparation of the various samples may advantageously employ the syringe battery 14 in diluting the sample, adding reagents, and the like. By using the syringe battery 14, all manipulations are identical to the manipulations employed with the standards.

The tips 90 supported by rack 116 are now introduced into insertion block 140, the syringe ends 86 introduced into the tips, and the syringe battery 14 pressed down so as to force the syringe ends to fit snugly into the tips.

The syringe battery 14 is then introduced into the motor driven housing 12 by sliding the syringe plunger plate 40 between the L-shaped arms 34 and 36 of the upper platform 32. A sample tray having the appropriate antibodies is placed on lower platform 50, with the upper platform 32 in its lowered position, so that the plungers extend a substantial distance downward into the syringes. Desirably, the syringes 84 may be partially filled with wash solution, so that after the antibodies are drawn up into the tips 90, the tips may be directly washed after ejection of the antibody solution by driving the plungers downward and expelling the wash solution through the tips. After a sufficient time, namely from about 1 to 16 hours, the contents of the tips are ejected into a waste tray and the tips washed twice, either with wash solution in the syringes 84, from the upper reservoir 118 or from wash solution in a sample tray. At the end of each maneuver, the tips are wiped and blotted.

The tips 90 are then ejected by means of ejection plate 96 and may be frozen or may be stored in a simple humidity controlled storage container 144 as depicted in FIG. 4.

The supporting control container 144 is an open-topped rectangular box 146 which supports the syringe battery 14, the syringe battery serving to enclose the box. A damp sponge 150 is included in the box to provide the desired humidity, so that the tips do not dry out.

Assuming the tips 90 have been retained on the syringe ends 86, the tray containing the samples and standards is now placed on the lower platform 50 and raised up, so that the tips reach substantially to the bottom of the cups 152. See FIG. 4. The appropriate amount of solution is then drawn up into the tips and the unit either left in the motorized housing 12 or transferred to the storage support box 144. Incubation of the samples is maintained under controlled temperature and humidity conditions.

The tips are then washed as indicated previously, a reagent tray containing radioactive antibodies placed on the lower platform 50 and raised so that the tips extend substantially the entire distance of the cups 152. The reagent is drawn up into the tips by raising the upper platform 40 and after sufficient time for binding of the antibody, the labelled antibody solution is ejected into a waste tray, and the tips washed, wiped and blotted dry.

A plurality of reagent solutions can be contained in the syringes and separated by gas bubbles. Thus, one can direct a series of different solutions through the tip by severally withdrawing reagents into the syringes from the sample trays alternately with drawing in air. The amount of spacing air should be sufficient to expel the solution from the tip. These spent solutions can be discarded by withdrawing into the reservoir.

The tips are then ejected again while still attached to the tip rack 116 into the insertion block. The tips are then inserted one by one in counting tubes for counting of the radioactivity attached to the inner wall of the tips. The amount of radioactivity on the tips is a direct function of the amount of analyte present in the standard or unknown solutions. By preparing a standard curve, one can compare the results with the unknowns to the standard curve to calculate the amount of the analyte in the unknown samples.

In similar fashion in accordance with the techniques which are applicable, other immunoassays may be carried out, such as RIA, IRMA, enzyme immunoassays, and the like.

While the subject apparatus has been illustrated as used in an immunoassay, the subject apparatus can be used in any situation where it is desirable to carry out numerous simultaneous transfers of liquids, so that the subject apparatus can be used for automated pipetting, sampling, aspiration, or the like.

EXPERIMENTAL (All temperatures not otherwise indicated are in Centigrade. All percents not otherwise indicated are weight percent.)

EXAMPLE A

USE OF ASSAY MACHINE FOR THE 2-SITE IMMUNORADIOMETRIC ASSAY (2-SITE IRMA) OF PLASMA HUMAN GROWTH HORMONE (HGH).

METHOD 1

1. Preparation of standards and unknowns

Standard solutions of HGH are made up in hormone-free human blood plasma diluted 1:5 with diluent (diluent = 0.05M sodium barbitane, 0.1M NaCl, 0.1% bovine serum albumin (BSA), and 0.01% sodium azide at pH = 8.0. This diluent is referred to as BSA-buffer.) Four replicates of each of 10 standards (0 - 10ng/ml) are stored in a 96 position plastic tray (Cooke Microtiter Ltd). Also in the tray are 6 replicates of each of 3 "quality control" human plasmas also diluted 1:5. These human plasmas ($Q_1$, $Q_2$ and $Q_3$) are chosen to represent the low, medium and high levels of circulating HGH, and are frozen away in many aliquots.

Human plasma samples of unknown HGH content are diluted 1:5 with diluent and assayed in duplicate. Any samples assayed at a dilution of more than 1:5 are diluted further with the 1:5 diluted hormone-free human plasma. After each 44 "unknown" tips, a duplicate "zero dose" standard and duplicate $Q_2$ samples are included.

These assay samples are prepared and diluted in the trays by using the assay machine as a sampler-diluter. The samples are stored frozen in the trays after being sealed by means of Cookes microtiter dispenser and tape.

2. Preparation of tips.

Each rack of tips is inserted on a unit using the insertion block. The tip support rack remains attached to the tips. The tips are "coated" with anti(HGH) by drawing up into the tips 120μl of guinea pig anti(HGH) serum diluted 1:4000 in sodium bicarbonate 0.2M pH 9.2. This antiserum is drawn up from a tray elevated under the tips. After 1-16 hours, the contents of the tips are ejected into the waste tray, and the tips washed twice from the wash reservoir. Each 120μl of wash solution is discarded into the waste tray. The wash solution contains phosphate buffer 0.05M, pH 8.0, 0.1% BSA, 0.45% NaCl and 0.01% $NaN_3$. At the end of each maneuver, the tips are wiped and blotted.

3. Storage of activated tips.

Alternatively, the tips containing 120μl of "coating" antiserum or wash solutions are frozen, and the tips ejected complete with the tip-support rack (using the tip ejection mechanism), to be stored frozen as a stack of tip-support racks in a plastic bag. These tips are thawed and reinstalled on the unit when required for assay.

4. Assay procedure.

a. Incubation of unknown and standard (Reaction 1).

The assay begins when the standards and unknown samples are simultaneously drawn-up into the "coated" and washed tips. One hundred and twenty microliters of solution is drawn up under programable electronic control using a minimal syringe air space. The unit is then either left in the motorized section or removed and placed in the storage support box. In either place, the incubation proceeds under controlled temperature and humidity.

b. First wash.

The tips are then washed in the same manner as described previously and the tips wiped and blotted.

c. Second reaction.

One hundred and twenty microliters of purified radioactive anti(HGH) is then drawn-up from a reagent tray. This reagent is diluted in the BSA buffer so that $120\mu l$ = 20000–40000cpm. The unit is reincubated as before.

d. Final wash.

After 24–48 hours the labelled antibody is ejected into the waste tray and the tips again washed and wiped or blotted dry.

5. Measuring the radioactivity on the tips.

The tips are ejected (still attached to the tip support plate), using the tip ejection mechanism into the insertion block. The tips are then inserted one by one in counting tubes for counting of the radioactivity attached to the inner wall of the tips, using an automatic gamma counter.

6. Data analysis.

The amount of radioactivity on the tips is a direct function of the amount of HGH present in the standard or unknown solutions.

A "standard curve" is constructed from the results of the assay of the HGH standards and the concentration of HGH in the unknown plasma is calculated by comparing the tube radioactivity of the unknowns with the tube radioactivity of the standards.

METHOD 2

Use of assay machine for the 2-site IRMA of plasma HGH-with washing from syringes.

This method is identical to Method 1 except that the syringes are filled with wash solution. The first and second reaction is carried out with the unknown or labelled antibody separated from the wash solution by an air bubble. All solutions contain a small amount of propylene glycol to reduce surface tension. At th end of each reaction the solid-phase is washed by ejecting the solution in the tips into the waste tray, followed by $200\mu l$ of wash solution which is ejected from the syringes and through the tips. New buffer may be introduced into the syringes via the syringe plungers via a chamber placed about the syringe barrels, or by aspirating from below.

METHOD 3

Use of assay machine for the 2-site IRMA of plasma HGH-with all solution being drawn through into the syringes.

This method is identical to Method 1 except that at the completion of each reaction the solution in the tips is drawn through the tips into the syringes. An air bubble-space is needed during reaction two in order to separate the waste solutions (in the syringes) from the labelled antibody (in the tips). All solutions contain a small amount of propylene glycol to reduce surface tension. Waste solution in the syringes may be evacuated through the plungers or through a chamber about the syringe barrels using mild suction.

METHOD 4

Use of assay machine for 2-site IRMA or HGH with repeated aliquots of unknown.

This assay procedure is identical to that described in Example 1 except that Assay Reaction 1 is carried out by taking repeated aliquots of unknown (eg. $120\mu l$ at hourly intervals). As a new aliquot is taken, the previous aliquot is drawn up into the syringe. Alternatively, the previous aliquot can be discarded into the waste tray. This method results in an assay of increased sensitivity.

METHOD 5

Use of assay machine for 2-site IRMA for HGH with slow continuous aspiration of unknown.

This assay procedure is identical to that described in Example 1 except that Assay Reaction 1 is carried out by reacting an unusually large amount of unknown. This is done by slowly and continuously aspirating the unknown solution through the tip into the syringe. This method concentrates the unknown from a larger volume for reaction with the labelled antibody (Reaction 2).

EXAMPLE B

Use of the Assay Machine for IRMA.

In the IRMA method, the unknown antigen is reacted with soluble purified radioactive antibodies. The radioactive complex remains in solution while unused radioactive antibodies are removed by a second reaction with a solid-phase antigen. The amount of radioactivity remaining in solution is a direct function of the antigen concentration. IRMA has also been adapted to the use of labelled anti-IgG as an additional 'universal' reagent, thereby avoiding the necessity for the preparation of radioactive antibodies specific for the unknown antigen.

The assay of HGH using IRMA is carried out in an analogous fashion to the procedures described for RIA and 2-site IRMA.

In IRMA, excess antigen is fixed into the solid-phase (tips), and the incubation mixture containing unknown antigen and purified labelled specific antibody, is drawn into the tips. Any labelled antibody not bound to soluble antigen is bound to the tips. The tips are washed and label bound to the tips is inversely related to the amount of antigen present in the unknown solution.

EXAMPLE C

Use of Assay Machine for RIA.

In RIA and the analogous competitive-binding assay techniques, there is competition between the unknown antigen and a labelled antigen derivative for a limiting amount of specific binding reagent (usually an antibody). Free labelled antigen is separated from the labelled antigen bound to antibody (or other specific binder) by a variety of procedures, but if the binding reagent is in a solid-phase, then unreacted labelled antigen can be simply washed away. The amount of labelled antigen bound to the binding reagent, is an inverse function of the concentration of unknown antigen. The assay can be carried out in a single reaction, or the labelled antigen can be added later as a "delayed" or "second" reaction. This maneuver is often referred to as "delayed addition of the trace", and frequently results in improved assay sensitivity. If the solid phase is washed free of unreacted, unknown-solution constituents before the addition of the "trace" (labelled antigen), then the labelled antigen will not directly encounter any possibly damaging or interfering constituents of the unknown solution.

In an alternative procedure, the labelled derivative (detectant) can be reacted with the solid phase antibody (insolubilized member) before the reaction with analyte. With hapten assays, this allows reproducible preliminary preparations without deterioration in dose response and may inhibit assay perturbations due to the presence of serum.

EXAMPLE D

USE OF ASSAY MACHINE FOR THE RIA OF CORTISOL IN HUMAN PLASMA.

METHOD 1

1. Preparation of standards, unknown and quality control samples.

Nine quadruplicate standards (zero to 5000ng/ml) are made up in a solution containing 0.05M phosphate buffer, pH = 8.0, containing 0.1% bovine serum albumin and 0.01% sodium azide. This solution is referred to as BSA-buffer. Quadruplicate quality control plasma samples (Q1, Q2, and Q3) were chosen to represent the low, medium and high levels of circulating plasma cortisol. Unknown plasma samples were assayed in duplicate. The $^{125}$I-cortisol was diluted in BSA-buffer.

The standards, quality control plasmas, and unknown plasma samples were diluted 1:21 with 95% ethanol. The resulting precipitate was centrifuged and an aliquot of the supernatant was diluted with $^{125}$I-cortisol. The final sample dilution was 1:399 and contained 6000cpm/100μl. This solution was stored in sample plates and covered with special film, to await the assay procedure.

2. Preparation of tips.

The tips were activated as described previously except that multiple layers of IgG were used. An initial coat of normal rabbit serum diluted 1:1000 in 0.2M NaHCO$_3$ (pH = 9.2) was followed by a coat of guinea pig anti(rabbit IgG) serum diluted 1:1000 in BSA-buffer. After 4 hours this solution is ejected and the tips washed twice with the BSA-phosphate buffer. The tips can now bind (insolubilize) any antiserum provided that it has been prepared in rabbits. In the cortisol assay, rabbit anti (cortisol) serum diluted 1:25,000 in BSA-buffer is aspirated into the tips and incubated for 16 hours before washing in BSA-buffer. All incubations are carried out an ambient temperatures.

The tips can be stored for later use by being frozen in racks while containing antibody solution or BSA-buffer. Tips stored before the final specific antibody has been reacted, can be used for any assay which uses a rabbit antiserum.

3. Assay procedure.

The solutions to be assayed (which also contain $^{125}$I-cortisol) are drawn up into the tips from the sample tray. The incubation is carried out at room temperature in the motorized section or the storage support box, under controlled temperature and humidity. After 16 hours the tips are evacuated, washed, and blotted dry before counting the radioactivity bound to the solid-phase. (Alternatively, the $^{125}$I-cortisol may not be mixed with the unknown but added later in a second reaction i.e. "delayed addition of the trace" or "preincubation of the trace".)

4. Dose Interpolation.

The amount of radioactivity bound to the tips is an inverse function of the amount of cortisol present in the standard or unknown solutions.

METHOD 2

Use of Assay Machine for RIA of cortisol using delayed addition of the trace and repeated aliquots of unknown.

This assay is carried out as described above except that repeated aliquots of unknown are taken and the unknown is not mixed with $^{125}$I-cortisol. The $^{125}$I-cortisol is drawn up as a second (later) reaction. This results in an assay of increased sensitivity.

METHOD 3

Use of Assay Machine for RIA of cortisol using delayed addition of the trace and a slow continuous aspiration of the unknown.

This assay is carried out as described in Example 2 except that the unknown is slowly and continuously aspirated through the tips into the syringes (as described for 2-site IRMA). This results in an assay of increased sensitivity.

In employing Method 1, in the determination of human growth hormone in hormone-free human plasma the following results were obtained.

TABLE 1

REPRODUCIBILITY OF ASSAY MACHINE.
2-site IRMA of human growth hormone in hormone-free human plasma diluted 1:5 with buffer — CV of response (radioactivity) throughout standard curve and quality control plasma; and minimal detectable dose (MDD). Incubation volume = 120μl.

| Conc of HGH (ng/ml) (replicates=4) | % CV = SD/mean × 100 Assay Number | | | | | | mean | CV of response |
|---|---|---|---|---|---|---|---|---|
| | 1 | 2 | 3 | 4 | 5 | 6 | | |
| 0.0 | 5.90 | 1.15 | 3.74 | 6.51 | 5.07 | 4.10 | 4.41 | responses were 800–2000cpm, so counting error accounts for 3.5–2.2% in this part of standard curve. (counting time = 1 minute) |
| .02 | 6.40 | 2.48 | 2.86 | 1.78 | 2.22 | 4.58 | 3.83 | |
| .05 | 4.20 | 3.22 | 2.97 | 4.91 | 3.09 | 3.70 | 3.68 | |
| .1 | 2.80 | 0.98 | 2.00 | 1.06 | 2.53 | 2.16 | 1.92 | |
| .2 | 0.73 | 4.46 | 2.27 | 1.78 | 2.82 | 1.34 | 2.23 | |
| .5 | 1.23 | 2.41 | 0.62 | 2.56 | 3.04 | 0.51 | 1.73 | |
| 1.0 | 1.55 | 2.24 | 1.52 | 3.69 | 1.44 | 1.87 | 2.02 | |
| 2.0 | 1.18 | 2.75 | 1.24 | 1.40 | 0.93 | 1.51 | 1.50 | |
| 5.0 | 3.63 | 1.02 | 1.37 | 1.42 | 3.53 | 1.60 | 2.09 | |
| 10.0 | 2.45 | 0.85 | 0.82 | 0.81 | 0.96 | 0.62 | 1.08 | |
| Quality control | | | | | | | | |

TABLE 1-continued
REPRODUCIBILITY OF ASSAY MACHINE.
2-site IRMA of human growth hormone in hormone-free human plasma diluted 1:5 with buffer — CV of response (radioactivity) throughout standard curve and quality control plasma; and minimal detectable dose (MDD). Incubation volume = 120μl.

| plasmas (replicates=6) mean | | | | | | | |
|---|---|---|---|---|---|---|---|
| 0.11ng/ml mean | 2.28 | 5.50 | 2.03 | 2.14 | 2.50 | 3.37 | 2.97 |
| 0.36ng/ml mean | 0.77 | 1.73 | 3.59 | 1.32 | 2.14 | 2.35 | 1.98 |
| 1.70ng/ml | 1.23 | 2.24 | 1.63 | 2.45 | 1.29 | 1.70 | 1.75 |
| Overall mean CV of response (all points) | | | | | | | 2.36 |
| mean with 3 lowest standards excluded | | | | | | | 1.93 |
| MDD of a duplicate determination (picograms/120μl) | | | | | | | Mean MDD |
| | 1.43 | 0.83 | 1.06 | 0.95 | 0.40 | 0.40 | 0.84 |

When employing Methods 4 and 5 of the 2-site IRMA technique as described previously, greatly enhanced sensitivity was achieved. In the standard curve, the spread in cpm of tube radioactivity between 10 and 100pg/ml for Method 1 was 300cpm. For Method 4, the spread was approximately 1200cpm, while in Method 5 the spread was about 1250cpm. Furthermore, the curves for Method 4 and 5 as compared to Method 1, have much steeper slopes in the 10 to 50pg/ml region. Thus, depending upon the need for accuracy and sensitivity, extremely low concentrations can be readily detected.

The subject method provides an extremely simple and sensitive technique for determining a wide variety of immunologically bindable substrates or other compounds for which there are known receptors. Manual manipulation is minimized, particularly in those areas where individual introduction of error can occur. In addition, by carrying out all transfers simultaneously with carefully calibrated and equivalent syringes, conditions which fluctuate with time do not affect the standards differently from the unknown. Thus, the standard determinations and standard curve gives results for identical conditions under which the unknowns were also determined.

In the subject invention, the method is carried out in an open-ended tube so that solutions can be introduced and withdrawn easily and without movement or disturbance of the tube. As contrasted with a simple test tube, with the open-end tube, there is no mechanical disturbance during the removal of solutions. Furthermore, in the open tube one can provide a column effect, so that rather than having an equilibrium between the insolubilized SBS and the analyte, one can introduce the unknown solution to new unreacted insolubilized SBS by drawing the solution up into the tip. Reagents and/or wash solutions can be introduced into the tip from the syringes and later discarded into a wash tray. The reagents and/or wash solutions can be introduced into the syringes from the reservoir about the syringes. Alternatively, the reagents, wash solutions and assay sample can be introduced into the tip from a tray and later drawn up into the syringes. The "used" sample, reagents and/or wash solutions can be discarded from the syringes by suction through the reservoir. Where necessary, successive solutions are separated by an air bubble spacer.

The apparatus of the subject invention provides a convenient method whereby a multiplicity of samples can be prepared in the tray, the samples introduced into preprepared tips, and the multiple assays carried out simultaneously and under identical conditions. By employing carefully calibrated and uniform syringes and plungers, extremely accurate and reproducible results can be obtained. Large or small sample volumes can be employed with efficient insolubilization of the analyte due to the large capacity in the tips.

The tips are extremely versatile in the role they play. By employing conical tips of small orifice and outer diameter at the orifice, the tips can be used to sample and aspirate extremely small volumes allowing for efficient transfer from the sample tray to the tip. The tip can be introduced into the sample without causing overflowing. The volume of the tip is sufficient to carry out the various reactions required by the assay and then can be used directly for measuring the detectant.

Prior to this invention devices used a single sampler. Adventitious material present in a sample could become deposited in the sampler subjecting all subsequent samples to a common error. In the subject invention such an occurrence is precluded.

In addition, the original organization of the samples and standards, if any, is maintained throughout the assay, so that each sample retains a particular position for ease of recording results, particularly by automated means.

Finally, in many instances the tips can be preprepared with all reagents in the tip, so that any measurements of reagent volumes by the technician at the laboratory is avoided, substantially precluding the introduction of human error.

Although the foregoing invention has been described in some detail by way of illustration and example for purposes of clarity of understanding, it will be obvious that certain changes and modifications may be practiced within the scope of the appended claims.

What is claimed is:

1. In a method for carrying out assays for the determination of the amount of analyte in a sample, where the analyte is a member of one of two families which comprise a pair of specific bindable substances, said assay employing an insolubilized member of said pair and a detectant which provides a physically determinable signal in proportion to the number of molecules of detectant present and is a member of one of said families, the improvement which comprises:

drawing a solution of analyte by means of a syringe into an open-ended tip demountably mounted on said syringe, said tip containing said insolubilized member, with the proviso that when said analyte can be bound to said tip, said analyte can be said insolubilized member;

introducing any solutions of detectant or other reagents and wash solutions into said tip from an outside source or from said syringe by means of said syringe;

removing said solutions from said tip by means of said syringe; and measuring by means of said physically determinable signal the amount of detectant insolubilized in said tip or removed from said tip as a measure of the amount of analyte in said sample.

2. A method according to claim 1, wherein said assay is an immunoassay, and said pair of specific bindable substances are ligand and antiligand.

3. A method according to claim 2, wherein said analyte is ligand, said insolubilized member is antiligand, which is in insufficient amount to bind all of said ligand and said detectant; and said detectant is radioactively labelled ligand.

4. A method according to claim 2, wherein said analyte is polyepitopic ligand; said insolubilized member is antiligand and is present in an amount in excess of the amount of ligand present; and said detectant is radioactively labelled anti-ligand.

5. A method according to claim 2, wherein said analyte is polyepitopic ligand; said insolubilized member is antiligand from a first species; and said detectant is a combination of antiligand from a second species and anti(antiligand) for said second species.

6. A method according to claim 2, wherein said insolubilized member is ligand and is present in an amount in excess of the amount of detectant present; said detectant is antiligand and is introduced concurrently into said tip with said analyte.

7. A method according to claim 2, wherein said insolubilized member is ligand present in an amount in excess of detectant present; said analyte is polyepitopic ligand; and said detectant is a combination of antiligand from a first species and radioactively labelled anti(antiligand) for said antiligand from said first species.

8. A method according to claim 2, wherein said insolubilized member is in excess of said analyte, and both said solution of analyte and solution of detectant are drawn through the tip into the syringe so as to continuously expose said solution of analyte to unbound insolubilized member.

9. A method according to claim 2, wherein said insolubilized member is antiligand and is present in excess of said analyte; and including the steps of:

removing said solution of analyte;

washing said tip with a wash solution prior to introduction of detectants;

drawing said solution of detectant into and through said tip by means of said syringe; and washing said tip to remove any non-specifically bound detectant.

10. A method for carrying out a plurality of assay determinations in a plurality of samples, where the analyte to be determined is a member of one of two families which comprise a pair of specifically bindable substances and at least one sample contains a known amount of said analyte; employing for said assay determinations: an insolubilized member of one of said families; a detectant which provides a physically determinable signal in proportion to the number of detectant molecules present and is a member of one of said families; and a battery of syringes with plungers connected for synchronous movement and tips demountably mounted on the ends of said syringes for receiving solution and retaining said insolubilized member which comprises:

simultaneously drawing into each of said tips containing said insolubilized member a different one of said samples;

introducing detectant solution or any other reagent solutions and wash solutions into said tips from an outside source or from syringes by means for said syringes;

removing said solution from said tips by means of said tips; and measuring by means of said physically determinable signal the amount of detectant insolubilized in said tips or removed from said tips, as a measure of the amount of analyte in each of said samples.

11. A method according to claim 10, including the step of insolubilizing said insolubilized member in said tip, by drawing into said tip by means of said syringe a solution containing said insolubilized member in soluble form, whereby said insolubilized member becomes bound to the surface of said tips.

12. A method according to claim 10, wherein said insolubilized member is in insufficient amount for binding all of said detectant and said analyte, and said detectant is radioactively labelled and is able to compete with said analyte for said insolubilized member.

13. A method according to claim 10, wherein said insolubilized member is present in excess of the amount of said analyte present, said detectant is radioactively labelled and said detectant and said insolubilized member are able to bind to said analyte.

14. A method according to claim 13, wherein said insolubilized member is antibody from a first species and said detectant is antiligand from a second species and radioactively labelled anti(antiligand) for said second species.

15. A method according to claim 10, wherein said insolubilized member is able to compete with said analyte for said detectant and said detectant is radioactively labelled, and wherein, said detectant and said analyte are combined prior to introduction into said tips.

16. A method according to claim 15, wherein said analyte and said insolubilized member are members of the same said family and are ligands selected from the group consisting of haptens and antigens, and said detectant is antiligand and radioactively labelled anti(antiligand).

17. An apparatus for carrying out a plurality of simultaneous transfer of liquids involving the introduction and explusion of solutions from small tips seated on tip receiving ends of syringes which comprises:

a housing having an upper and lower platform;

retained between said upper and lower platforms in predetermined spatial relationship, a plurality of syringe cylinders having tip receiving ends extending from said cylinders through said lower platform, each of said syringe cylinders having at least one port in an upper portion of said cylinders;

a fluid reservoir in fluid connection with said ports;

a plurality of syringe plungers housed in said syringe cylinders, said plungers having rods extending above said upper platform;

means for simultaneously moving said plungers in a vertical direction connected to an upper portion of said plungers; and means for simultaneously unseating a plurality of said tips from said syringe ends mounted between said lower platform and the upper edge of said tips seated on said syringe ends.

18. An apparatus according to claim 17, wherein said syringe plungers have hollow centers.

19. An apparatus according to claim 17, wherein said means for unseating said tips comprises a plate having a plurality of openings through which said syringe ends extend; cam means operably connected to said plate for lowering said plate to eject said tips; and resilient means for restoring said plate to its rest position.

20. An apparatus for receiving and controlling an apparatus for carrying out a plurality of simultaneous transfers of liquids involving the introduction and explusion of solutions from small tips seated on tip receiving ends of syringes comprising:
a frame;
a housing having an upper and lower platform adapted for removable mounting in said frame;
retained between said upper and lower platforms in predetermined spatial relationship, a plurality of syringe cylinders having tip receiving ends extending from said cylinders through said lower platform, each of said syringe cylinders having at least one port in an upper portion of said cylinders;
a fluid reservoir in fluid connection with said ports;
a plurality of syringe plungers housed in said syringe cylinders, said plungers having rods extending above said upper platform;
means for simultaneously moving said plungers in a vertical direction connected to an upper portion of said plungers;
means for simultaneously unseating a plurality of said tips from said syringe ends mounted between said lower platform and the upper edge of said tips seated on said syringe ends;
holding means for rigidly holding said plunger moving means in an upper portion of said frame;
supporting and restraining means for holding said lower platform in a stationary position in a lower portion of said frame;
raising and lowering means operably connected to said plunger holding means for raising and lowering said plungers to predetermined positions; and
power means connected to said raising and lowering means.

21. An apparatus according to claim 20, including a supporting platform below said maintaining means for said lower platform.

22. An apparatus according to claim 21, including raising and lowering means operably connected to said supporting platform.

23. An apparatus according to claim 20, wherein said raising and lowering means for said plunger moving means comprises:
a plurality of threaded rods threadably engaging said holding means for said plunger moving means; and
gear means operatively connected to said power means in driving engagement with said threaded support rods.

24. An apparatus according to claim 20, wherein said raising and lowering means for said holding means is hydraulic means.

25. An apparatus according to claim 20, including programmed control means operably connected to said power means.

26. An apparatus according to claim 20, wherein said syringe plungers have hollow centers.

27. A small conical tip for use in immunossays and mounting on syringe ends having a plurality of spacer arms bound to the inner surface of said tip capable of covalent or non-covalent binding to proteins and polypeptides.

28. A conical tip according to claim 27, wherein said spacer arms are antiligand.

29. A conical tip according to claim 27, wherein said spacer arms have functional groups capable of reacting with amino groups of said proteins and polypeptides to form amide or amidine linkages.

30. A conical tip according to claim 27 having a lower orifice diameter in the range of 0.25 to 2mm.

31. A conical tip according to claim 27 having an uneven inner surface.

* * * * *